United States Patent
Goodman et al.

(10) Patent No.: US 9,071,896 B2
(45) Date of Patent: Jun. 30, 2015

(54) SOUND PROCESSOR HOUSINGS, SOUND PROCESSORS AND IMPLANTABLE COCHLEAR STIMULATION SYSTEMS INCLUDING THE SAME

(75) Inventors: James P. Goodman, Valencia, CA (US); Adam Smith, Palm Desert, CA (US)

(73) Assignee: Advanced Bionics AG, Staefa (CH)

( * ) Notice: Subject to any disclaimer, the term of this patent is extended or adjusted under 35 U.S.C. 154(b) by 270 days.

(21) Appl. No.: 13/989,405

(22) PCT Filed: Nov. 19, 2011

(86) PCT No.: PCT/US2011/061562
§ 371 (c)(1),
(2), (4) Date: Jul. 27, 2013

(87) PCT Pub. No.: WO2012/082319
PCT Pub. Date: Jun. 21, 2012

(65) Prior Publication Data
US 2013/0301852 A1    Nov. 14, 2013

Related U.S. Application Data

(60) Provisional application No. 61/424,565, filed on Dec. 17, 2010.

(51) Int. Cl.
| | |
|---|---|
| H04R 25/00 | (2006.01) |
| H04R 1/02 | (2006.01) |
| A61N 1/00 | (2006.01) |
| F16J 15/34 | (2006.01) |
| H01M 2/10 | (2006.01) |
| A61N 1/36 | (2006.01) |
| A61N 1/375 | (2006.01) |

(52) U.S. Cl.
CPC ............. *H04R 1/02* (2013.01); *A61N 1/36032* (2013.01); *A61N 1/375* (2013.01); *H01M 2/1038* (2013.01); *H01M 2220/30* (2013.01); *H04R 25/602* (2013.01)

(58) Field of Classification Search
None
See application file for complete search history.

(56) References Cited

U.S. PATENT DOCUMENTS

| | | | |
|---|---|---|---|
| 4,456,797 A | 6/1984 | Olsen | |
| 4,562,590 A | 12/1985 | DeLage | |
| 4,584,718 A | 4/1986 | Fuller | |
| 4,682,363 A | 7/1987 | Goldfarb et al. | |
| 4,683,587 A | 7/1987 | Silverman | |
| 4,727,599 A | 2/1988 | Rappaport et al. | |
| 4,918,737 A | 4/1990 | Luethi | |
| 5,294,988 A | 3/1994 | Wakabayashi et al. | |
| 5,386,084 A | 1/1995 | Risko | |
| 5,625,688 A | 4/1997 | Ford et al. | |

(Continued)

FOREIGN PATENT DOCUMENTS

| | | |
|---|---|---|
| DE | 102007061313 A1 | 6/2009 |
| DE | 102009010376 A1 | 4/2010 |

(Continued)

OTHER PUBLICATIONS

PCT Search Report and Written Opinion dated May 10, 2012 for PCT App. Ser. No. PCT/US2011/061562.

*Primary Examiner* — Andrew L Sniezek
(74) *Attorney, Agent, or Firm* — Henricks, Slavin & Holmes LLP

(57) ABSTRACT

Sound processor housings, sound processors and systems including sound processors are disclosed.

17 Claims, 11 Drawing Sheets

(56) References Cited

U.S. PATENT DOCUMENTS

| | | | |
|---|---|---|---|
| 5,704,803 A | 1/1998 | Oshima | |
| 5,818,946 A | 10/1998 | Walter | |
| 5,824,022 A | 10/1998 | Zilberman et al. | |
| 5,896,453 A | 4/1999 | Speaks | |
| 6,041,128 A | 3/2000 | Narisawa et al. | |
| 6,092,707 A | 7/2000 | Bowes, Jr. | |
| 6,396,769 B1 | 5/2002 | Polany | |
| 6,614,722 B2 | 9/2003 | Polany et al. | |
| 6,831,988 B2 | 12/2004 | Vonlanthen | |
| 6,954,405 B2 | 10/2005 | Polany et al. | |
| 7,069,063 B2 | 6/2006 | Halkosaari et al. | |
| D528,213 S | 9/2006 | Darley et al. | |
| 7,158,376 B2 | 1/2007 | Richardson et al. | |
| 7,194,101 B2 | 3/2007 | Vonlanthen | |
| 7,248,712 B2 | 7/2007 | Gabathuler | |
| 7,263,032 B2 | 8/2007 | Polany et al. | |
| 7,312,984 B2 | 12/2007 | Richardson et al. | |
| 7,394,911 B2 | 7/2008 | Joergensen et al. | |
| 7,400,917 B2 | 7/2008 | Wood et al. | |
| 7,440,579 B2 | 10/2008 | Vonlanthen | |
| 7,486,992 B2 | 2/2009 | Pufulescu et al. | |
| 7,503,790 B2 | 3/2009 | Bodmann et al. | |
| 7,535,799 B2 | 5/2009 | Polany et al. | |
| 8,965,019 B2 * | 2/2015 | Goodman | 381/322 |
| 8,965,020 B2 * | 2/2015 | Goodman | 381/322 |
| 2002/0119697 A1 | 8/2002 | Chan | |
| 2002/0193136 A1 | 12/2002 | Halkosaari et al. | |
| 2005/0181745 A1 | 8/2005 | Wood et al. | |
| 2007/0106344 A1 | 5/2007 | Darley et al. | |
| 2007/0270180 A1 | 11/2007 | Takagi | |
| 2008/0165996 A1 | 7/2008 | Saito et al. | |
| 2008/0273730 A1 | 11/2008 | Kral | |
| 2008/0288022 A1 | 11/2008 | Van der Borght et al. | |
| 2008/0298627 A1 | 12/2008 | Bonebright et al. | |
| 2009/0008880 A1 | 1/2009 | Bodmann et al. | |
| 2009/0017884 A1 | 1/2009 | Rotschild | |
| 2009/0092270 A1 | 4/2009 | Ho et al. | |
| 2009/0239135 A1 | 9/2009 | Wang et al. | |
| 2009/0325046 A1 | 12/2009 | Yang | |
| 2010/0226519 A1 | 9/2010 | Spragge | |

FOREIGN PATENT DOCUMENTS

| | | |
|---|---|---|
| EP | 1271898 A1 | 1/2003 |
| EP | 1271898 B1 | 4/2006 |
| GB | 2133133 A | 7/1984 |
| WO | WO 98/50281 A1 | 11/1998 |
| WO | WO 2005/062668 A1 | 7/2005 |
| WO | WO 2006/071210 A1 | 7/2006 |
| WO | WO 2007/102158 A2 | 9/2007 |
| WO | WO 2008/150642 A1 | 12/2008 |
| WO | WO 2009/063096 A2 | 5/2009 |

\* cited by examiner

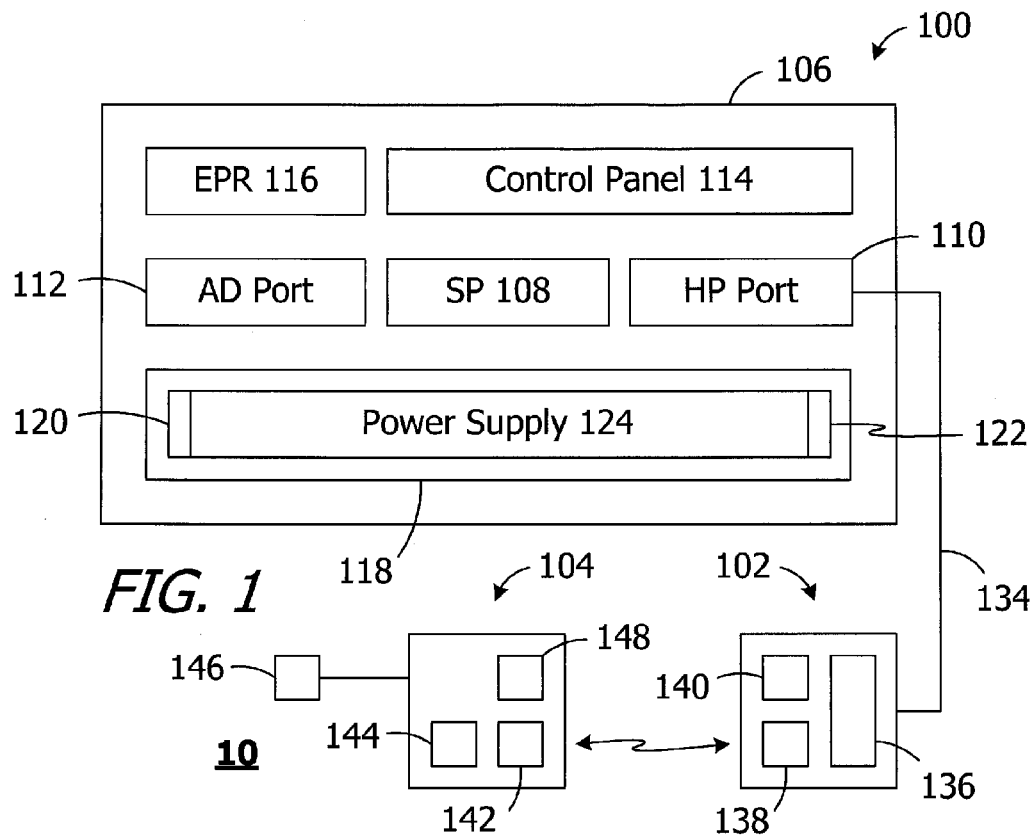
FIG. 1
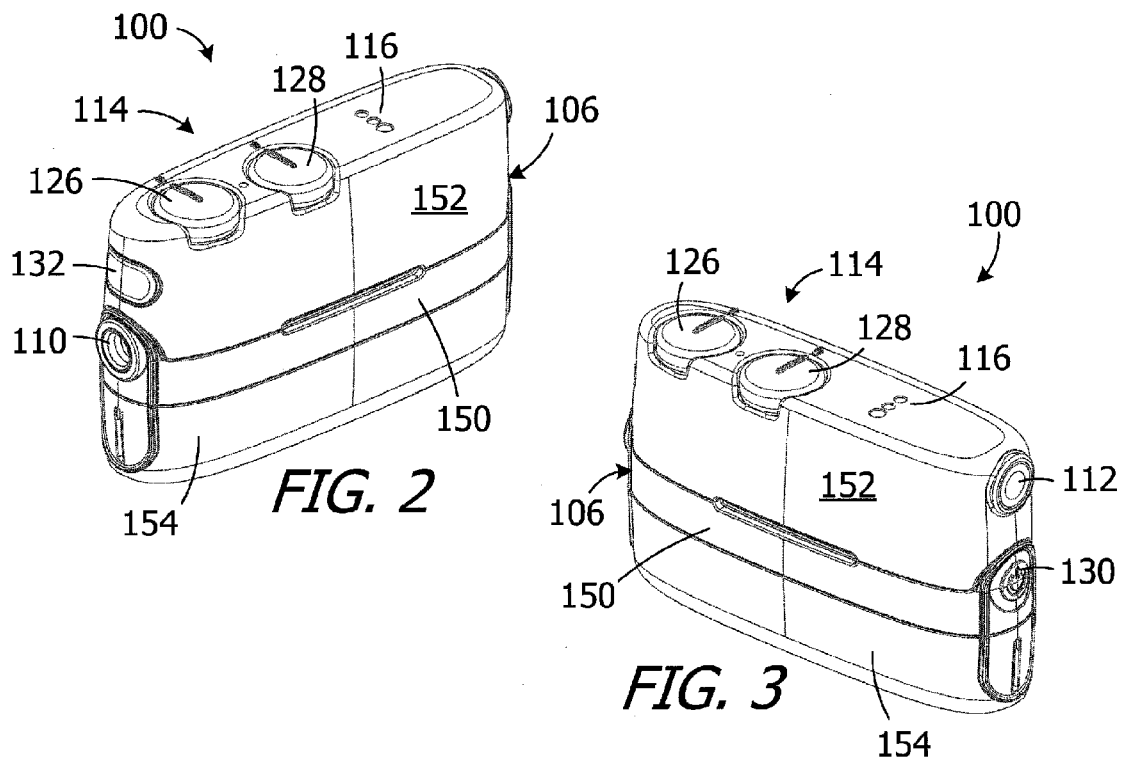
FIG. 2
FIG. 3

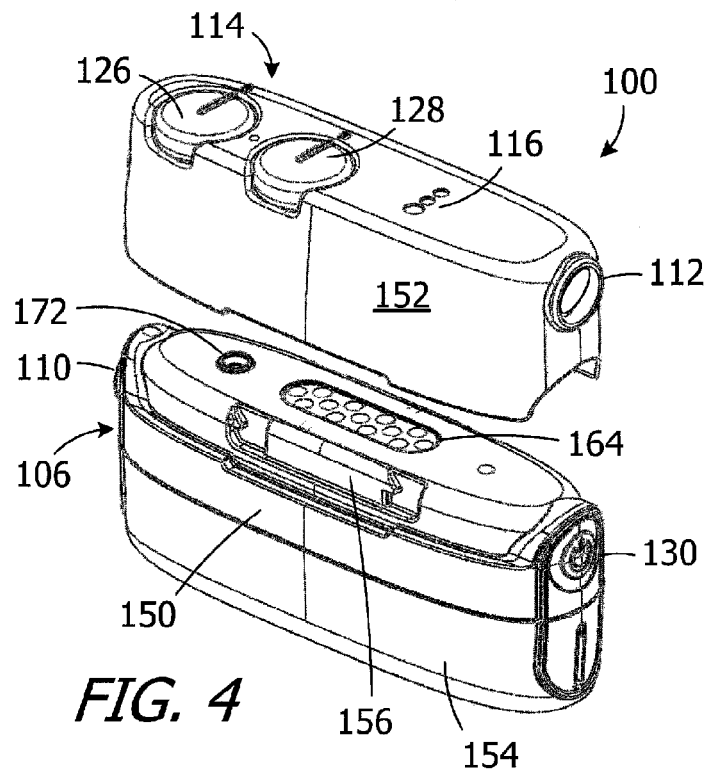
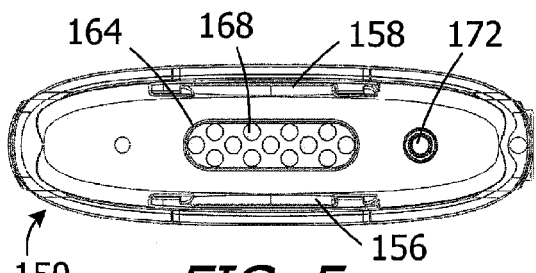
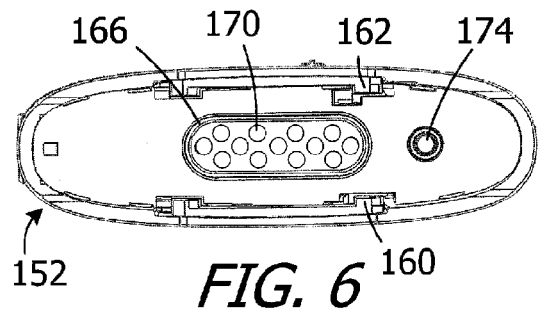
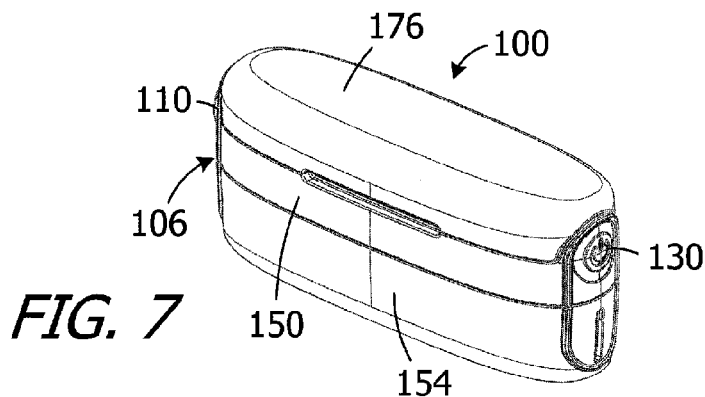

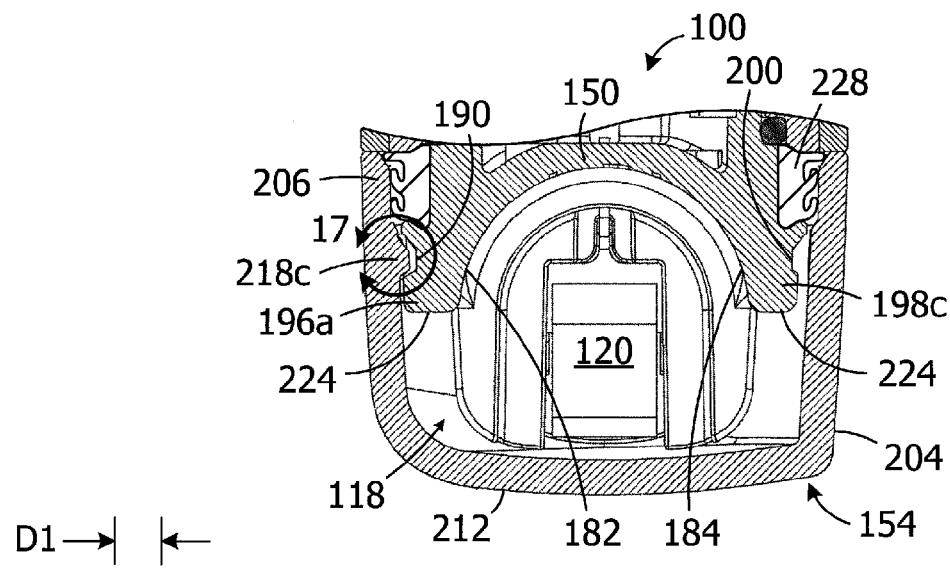
FIG. 14
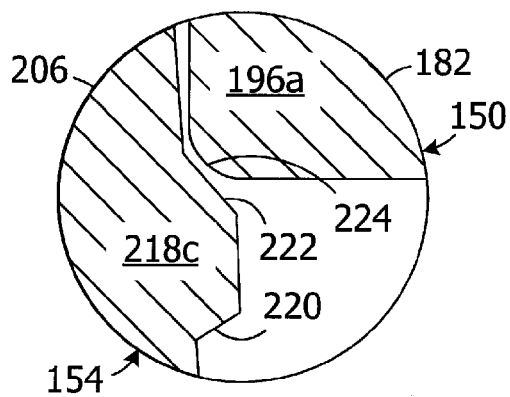
FIG. 15
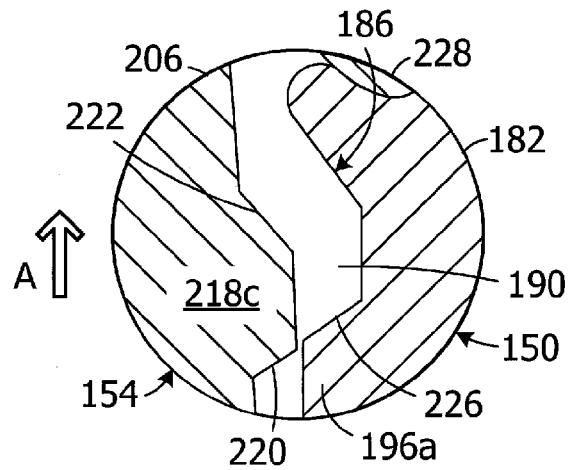
FIG. 16
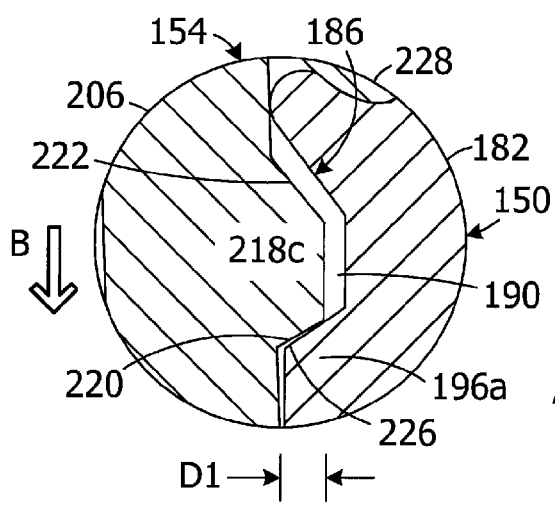
FIG. 17

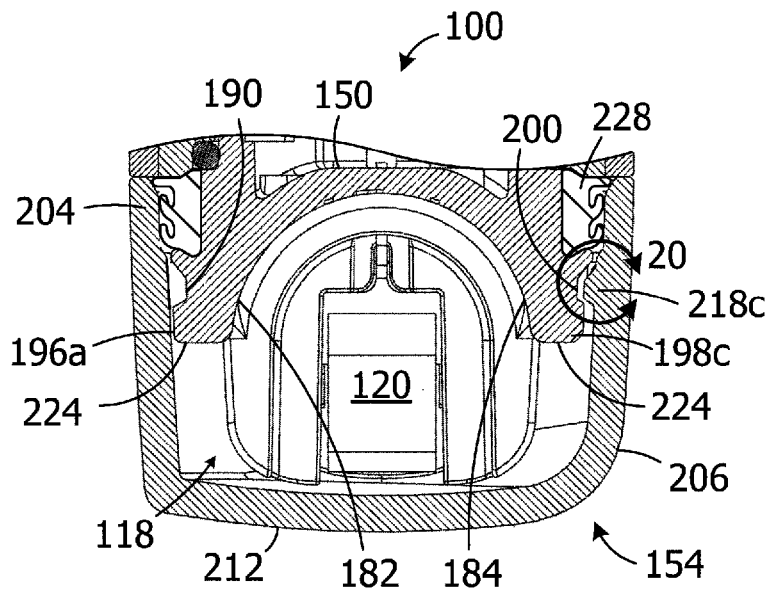
FIG. 18
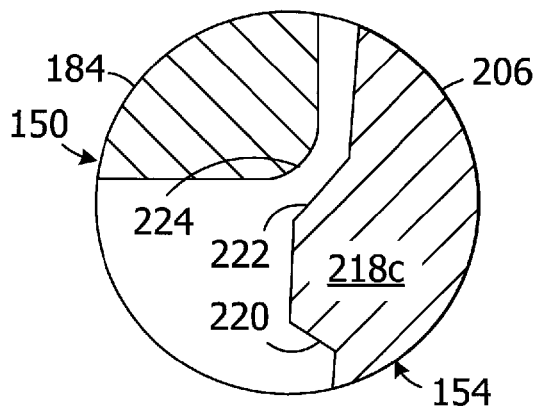
FIG. 19
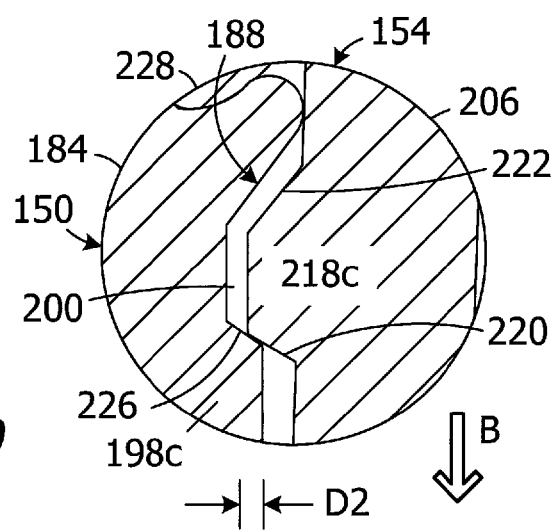
FIG. 20

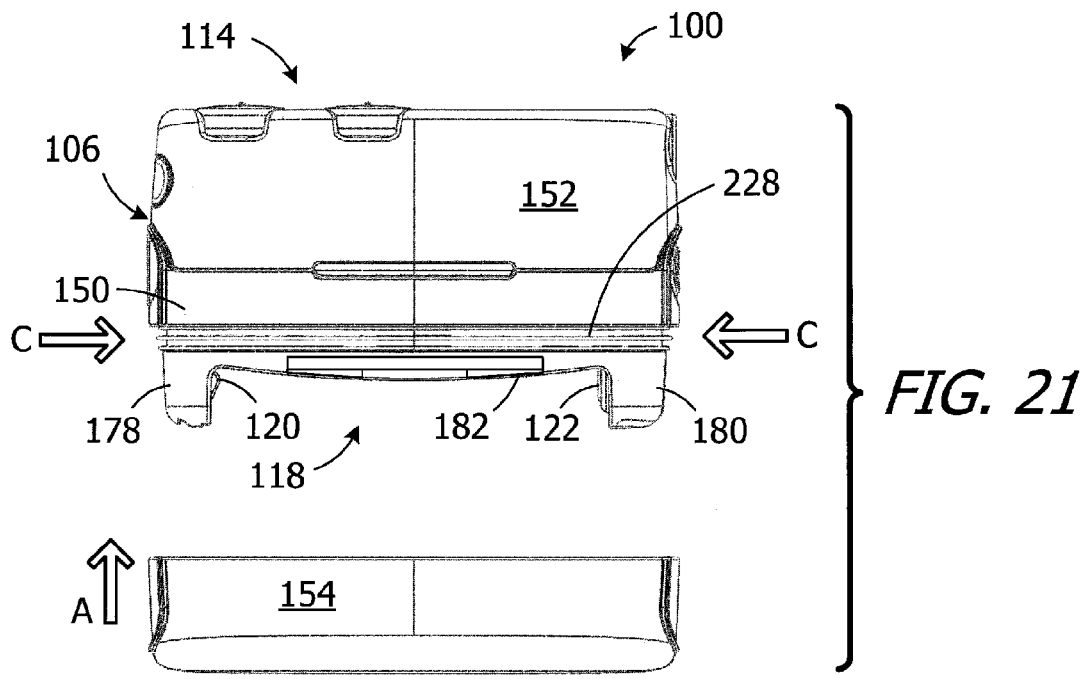
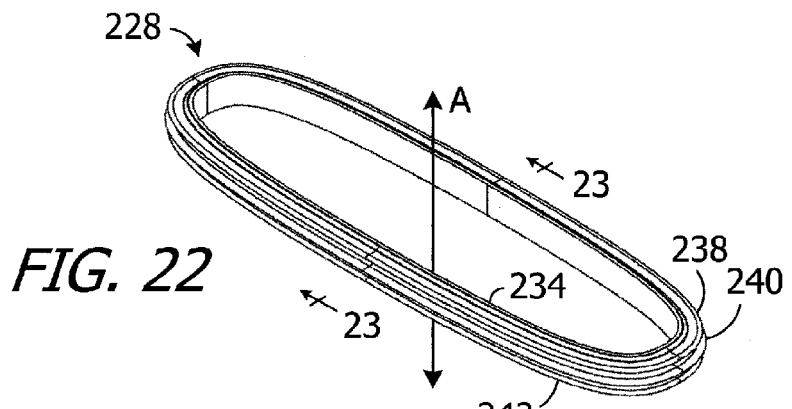
FIG. 22
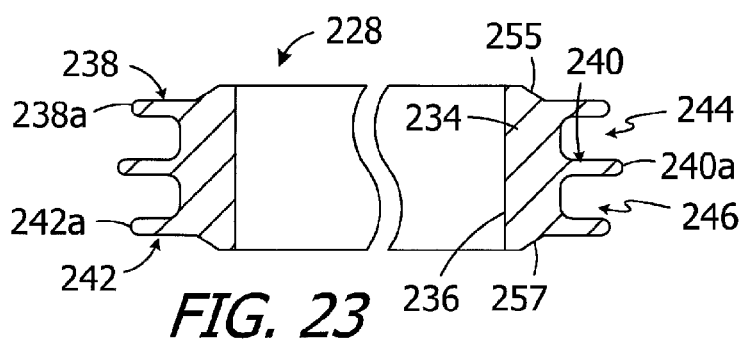
FIG. 23
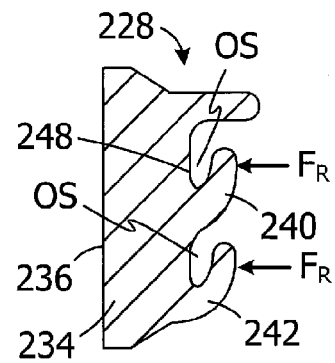
FIG. 23A

SOUND PROCESSOR HOUSINGS, SOUND PROCESSORS AND IMPLANTABLE COCHLEAR STIMULATION SYSTEMS INCLUDING THE SAME

CROSS-REFERENCE TO RELATED APPLICATIONS

This application is the U.S. National Stage of PCT App. Ser. No. PCT/US2011/061562, filed Nov. 19, 2011, which claims priority U.S. Prov. App. Ser. No. 61/424,565, filed Dec. 17, 2010.

BACKGROUND

1. Field

The present disclosure relates generally to sound processors such as, for example, the sound processors in implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound processor With Remote Control" and incorporated herein by reference in its entirety.

As alluded to above, some ICS systems include an implantable device, a sound processor unit, and a microphone that is in communication with the sound processor unit. The implantable device communicates with the sound processor unit and, to that end, some ICS systems include a headpiece that is in communication with both the sound processor unit and the implantable device. In one type of ICS system, the sound processor unit is worn behind the ear (a "BTE unit"), while other types of ICS systems have a body worn sound processor unit (or "body worn unit"). The body worn unit, which is larger and heavier than a BTE unit, is typically worn on the user's belt or carried in the user's pocket. In those instances where body worn units have a replaceable battery, the body worn unit housing will have a battery compartment (or "receptacle") and a removable battery compartment cover. One example of a conventional body worn unit is the Advanced Bionics Platinum Series body worn unit.

Body worn units may be preferable to BTE units in a number of instances. For example, BTE units tend to be too big for infants, and toddlers tend to remove and/or damage BTE units. Body worn units, on the other hand, can be attached to a harness that positions the sound processor unit on the infant or toddler's back, where it is difficult for the infant or toddler to reach. Many adults prefer BTE units for most everyday activities, but prefer body worn units for sports and other activities.

The present inventor has determined that conventional body worn units are susceptible to improvement. For example, the present inventor has determined that there are some instances where it is desirable for the removal of a battery compartment cover to be relatively difficult (e.g. require a relatively large removal force) and other instances where it is desirable for the battery compartment cover to be relatively easy to remove (e.g. require a relatively small removal force). For example, a battery compartment cover that is relatively difficult to remove may useful in those instances where the body worn unit is worn by a small child or a person doing rigorous exercise or swimming, while a battery compartment cover that is relatively easy to remove may be well suited for an adult in other settings as well as adults with limited dexterity.

SUMMARY

A sound processor housing in accordance with at least one of the present inventions includes a main portion with a power supply receptacle, a power supply receptacle cover, and a connector arrangement configured to connect the cover to the main portion with different levels of connection force depending upon the orientation of the cover relative to the main portion. The present inventions also include sound processors with such a housing, and cochlear stimulation systems with a cochlear implant and a sound processor with such a housing.

A sound processor housing in accordance with at least one of the present inventions includes a main portion with a power supply receptacle, a power supply receptacle cover, and structure that latches the cover to the main portion with different levels of connection force depending upon the orientation of the cover relative to the main portion. The present inventions also include sound processors with such a housing, and cochlear stimulation systems with a cochlear implant and sound processors with such a housing.

Such housings, sound processors and systems are advantageous for a variety of reasons. For example, the amount of force required to remove the power supply receptacle cover from the main portion may be varied by simply changing the orientation of the cover relative to the housing. As such, the same housings, sound processors and systems can readily accommodate the needs of children, adults with limited dexterity, active adults, and others.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a functional block diagram of an ICS system in accordance with one embodiment of a present invention.

FIG. 2 is a perspective view of a sound processor in accordance with one embodiment of a present invention.

FIG. 3 is a perspective view of a sound processor in accordance with one embodiment of a present invention.

FIG. 4 is an exploded perspective view of a sound processor in accordance with one embodiment of a present invention.

FIG. 5 is a plan view of a portion of a sound processor in accordance with one embodiment of a present invention.

FIG. 6 is a plan view of a portion of a sound processor in accordance with one embodiment of a present invention.

FIG. 7 is a perspective view of a sound processor in accordance with one embodiment of a present invention.

FIG. 14 is a section view of a portion of a sound processor in accordance with one embodiment of a present invention with the power supply receptacle cover in the latched position and in a first orientation.

FIG. 15 is an enlarged view showing the power supply receptacle cover in the first orientation spaced from the latched position.

FIG. 16 is an enlarged view showing the power supply receptacle cover in the first orientation spaced from the latched position.

FIG. 17 is an enlarged view of a portion of FIG. 14.

FIG. 18 is a section view of a portion of a sound processor in accordance with one embodiment of a present invention with the power supply receptacle cover in the latched position and in a second orientation.

FIG. 19 is an enlarged view showing the power supply receptacle cover in the second orientation spaced from the latched position.

FIG. 20 is an enlarged view of a portion of FIG. 18.

FIG. 21 is an exploded side view of a sound processor in accordance with one embodiment of a present invention.

FIG. 22 is a perspective view of a seal in accordance with one embodiment of a present invention.

FIG. 23 is a section view taken along line 23-23 in FIG. 22.

FIG. 23A is a section view showing a portion of seal illustrated in FIG. 23 in a radially compressed state.

DETAILED DESCRIPTION OF THE EXEMPLARY EMBODIMENTS

Figure 8:
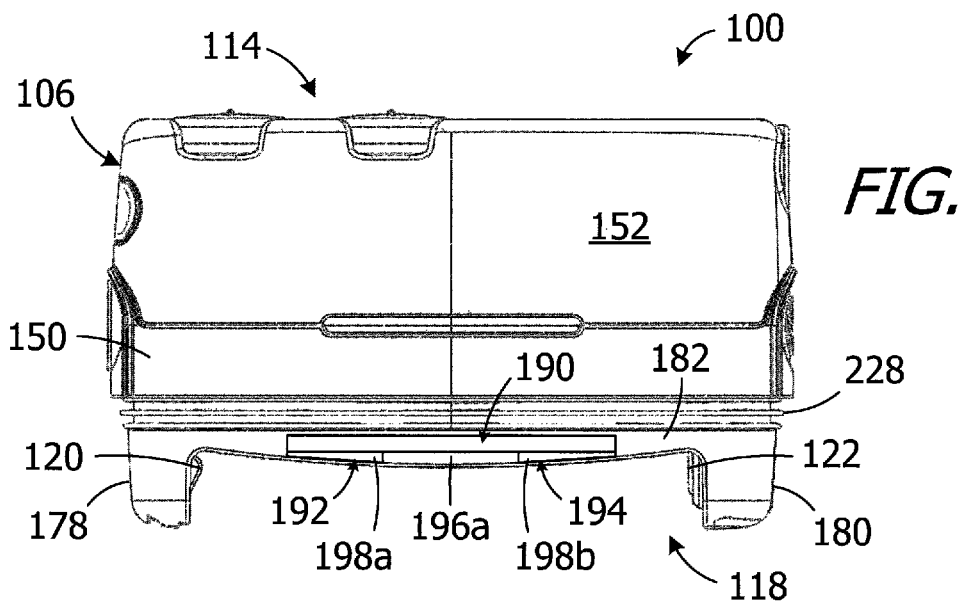
FIG. 8 is a side view of a portion of a sound processor in accordance with one embodiment of a present invention.

The following is a detailed description of the best presently known modes of carrying out the inventions. This description is not to be taken in a limiting sense, but is made merely for the purpose of illustrating the general principles of the inventions.

The present inventions have application in a wide variety of systems that provide sound (i.e. either sound or a perception of sound) to the hearing impaired as well as others who require such systems on a situational basis. One example of such a system is an ICS system where an external sound processor communicates with a cochlear implant and, accordingly, the present inventions are discussed in the context of ICS systems. The present inventions are not, however, limited to ICS systems and may be used in combination with other systems for the hearing impaired that currently exist, or are yet to be developed.

One example of a body worn sound processor ("sound processor") is generally represented by reference numeral 100 in FIGS. 1-3. The exemplary sound processor 100, which may be combined with a headpiece 102 and a cochlear implant 104 to form an ICS system 10, includes a housing 106 in which and/or on which various components are supported. Such components may include, but are not limited to, sound processor circuitry 108, a headpiece port 110, an auxiliary device port 112 for an auxiliary device such as a mobile phone or a music player, a control panel 114, a Euro Plug receptacle 116 (for a Euro Plug such as that associated with the Phonak MLxi FM receiver), and a power supply receptacle 118 with electrical contacts 120 and 122 for a removable battery or other removable power supply 124 (e.g. rechargeable and disposable batteries or other electrochemical cells). Power supply receptacles are also sometimes referred to as "battery compartments" when they are intended for use with a battery. The headpiece port 110 and auxiliary device port 112 may be connected to the sound processor circuitry 108 by way of, for example, a signal splitter/combiner (not shown) such as that found in the Platinum Signal Processor body worn unit from Advanced Bionics Corporation. In the illustrated embodiment, the control panel 114 includes a volume knob 126 and a program switch 128. A power button 130 and a bayonet release button 132 are also carried on the housing 106. The bayonet release button 132 actuates a bayonet mechanism to release the housing control portion 152 from the housing main portion 150 (described below).

The headpiece 102 in the exemplary ICS system 10 includes a cable 134 which may be connected to the headpiece port 110, a microphone 136, an antenna 138 and a positioning magnet 140. The exemplary cochlear implant 104 includes an antenna 142, an internal processor 144, a cochlear lead 146 with an electrode array, and a positioning magnet (or magnetic material) 148. The transmitter 138 and receiver 142 communicate by way of electromagnetic induction, radio frequencies, or any other wireless communication technology. The positioning magnet 140 and positioning magnet (or magnetic material) 148 position the headpiece antenna 138 over the cochlear implant antenna 142. During use, the microphone 136 picks up sound from the environment and converts it into electrical impulses, and the sound processor 100 filters and manipulates the electrical impulses and sends the processed electrical signals through the cable 134 to the transmitter 138. Electrical impulses received from an auxiliary device are processed in essentially the same way. The receiver 142 receives signals from the transmitter 138 and sends the signals to the cochlear implant internal processor 144, which modifies the signals and passes them through the cochlear lead 146 to the electrode array. The electrode array may be wound through the cochlea and provides direct electrical stimulation to the auditory nerves inside the cochlea. This provides the user with sensory input that is a representation of external sound waves which were sensed by the microphone 136.

It should be noted that, in other implementations, communication between the sound processor and a headpiece and/or auxiliary device may be accomplished through wireless communication techniques. It should also be noted that, in other implementations, the sound processor may be configured to directly communicate with the cochlear implant (i.e. without a headpiece and associated cable).

The exemplary sound processor 100 may be carried by the user in a variety of ways. By way of example, but not limitation, the sound processor 100 may be carried in the user's pocket, secured to a belt with a belt clip that is either part of housing 106 or a separate carrier, or placed in a harness that is configured to be worn by a small child.

Referring more specifically to FIGS. 2 and 3, the exemplary housing 106 includes a main portion 150, a control portion 152 and a power supply receptacle cover ("PSR cover") 154 that may be latched or otherwise detachably connected to the housing main portion 150 in the manner described below. The housing main portion 150 supports and/or houses the sound processor circuitry 108, headpiece port 110 and power button 130, and includes the power supply receptacle 118. The control portion 152 supports and/or houses the auxiliary device port 112, control panel 114, Euro Plug receptacle 116 and bayonet release button 132. In other words, in the exemplary implementation, the main portion 150 supports and/or houses those elements of the sound processor 100 that are required for the ICS system 10 to function, while the control portion 152 includes various elements that are only required from time to time (e.g. the volume knob 126) or are merely useful options (e.g. the auxiliary device port 112).

In the exemplary implementation, the sound processor 100 is configured such that the housing control portion 152 (and the functional elements associated therewith) may be mechanically and electrically separated from the housing main portion 150 (and the functional elements associated therewith) in the manner illustrated in FIG. 4. To that end, and referring also to FIGS. 5 and 6, the housing main portion 150 includes mechanical connectors 156 and 158 that are configured to mate with corresponding connectors 160 and 162 on the housing control portion 152. The housing main portion 150 and control portion 152 also include electrical connectors 164 and 166 with a plurality of contacts 168 and 170. An alignment locater feature, such as a post 172 and an opening 174 that receives the post and keys orientation, is also provided. Turning to FIG. 7, the sound processor 100 also includes a cover 176, with the same mechanical connectors (not shown) as the control portion 152, that may be used to protect the electrical connector 164 when the control portion is not in use.

It should also be noted here that, in other implementations, the sound processor may be configured such that the housing main portion and housing control portion define a single, integral unit that may not be separated in the manner described above.

Figure 9:
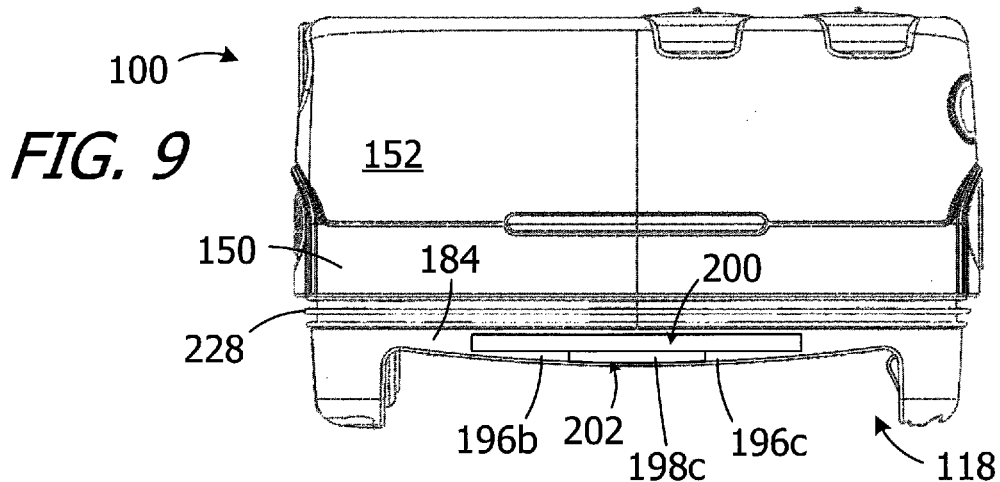
FIG. 9 is a side view of a portion of a sound processor in accordance with one embodiment of a present invention.

As illustrated in FIGS. 8 and 9, the power supply receptacle 118 in the exemplary embodiment is defined by various portions of the housing main portion 150. In particular, the housing main portion 150 has a pair of end walls 178 and 180 and a pair of side walls 182 and 184 that together define the volume, or at least a portion of the volume, in which a battery or other power supply is held. The electrical contacts 120 and 122 are carried on the end walls 178 and 180 and, in the exemplary embodiment, contact 120 is a resilient contact that is depressed as the battery or other power supply is positioned between the contacts. The resilient contact 120 presses against the battery or other power supply to hold it in place.

The exemplary sound processor 100 also includes structure that performs the functions of connecting (or "latching") the housing main portion 150 and the PSR cover 154 to one another in such a manner that the level of force required to disconnect (or "unlatch") the PSR cover from the housing main portion and/or connect (or "latch") the PSR cover to the housing main portion will vary based on the orientation of the PSR cover relative to the housing main portion. In the illustrated embodiment, the housing main portion 150 and PSR cover 154 are provided with respective structures, which together define a latch arrangement, that connect the main portion and PSR cover to one another with different levels of connection force depending upon orientation.

To that end, the exemplary housing main portion 150 includes first and second housing connectors 186 and 188 (FIG. 10) formed in the side walls 182 and 184, while the PSR cover 154 includes a connector 217 (FIGS. 11-13C). The connectors latch the housing main portion 150 and PSR cover 154 to one another in the manner described in greater detail below with reference to FIGS. 14-20.

Figure 10:
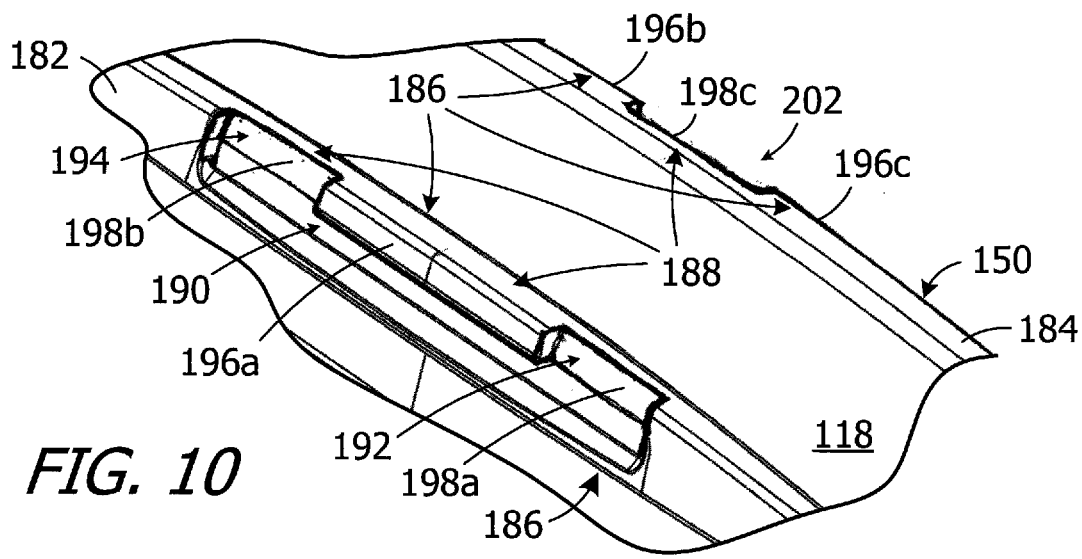
FIG. 10 is a perspective view of a portion of a sound processor in accordance with one embodiment of a present invention.

Referring more specifically to FIGS. 8-10, the first and second housing connectors 186 and 188 in the exemplary implementation each have portions that are located on opposite sides of the housing main portion 150. The first and second housing connectors 186 and 188 have different configurations. In particular, in the illustrated embodiment, the connectors 186 and 188 are defined by a plurality of indentations, with some indentations being deeper than others. In side wall 182, there is a primary indentation 190 and a pair of spaced secondary indentations 192 and 194. The primary indentation 190 is relatively deep as compared to the secondary indentations 192 and 194. The indentations 190-194 together define a relatively large latching protrusion 196a and a pair of relatively small latching protrusions 198a and 198b. Side wall 184 includes a primary indentation 200 and a secondary indentation 202. The primary indentation 200 is relatively deep as compared to the secondary indentation 202. The indentations 200 and 202 together define a pair of relatively large latching protrusion 196b and 196c and a relatively small latching protrusion 198c. The first connector 186 is defined by the indentations 190 and 200 and the relatively large protrusions 196a-196c, while the second connector 188 is defined by the indentations 190 and 200 and the relatively small protrusions 198a-198c. View another way, the indentations 190 and 200 are relatively deep at the protrusions 196a-196c and are relatively shallow at the protrusions 198a-198c due to the locations of the indentations 192, 194 and 202.

As illustrated for example in FIGS. 11-13C, the PSR cover 154 in the exemplary implementation includes side walls 204 and 206, end walls 208 and 210, a bottom wall 212 and an open end 214 opposite the bottom wall. The intersections of the side and end walls 204-210, and to some extent the side and end walls themselves, are curved. The cover walls in other implementations may define a rectangular shape with 90 degree corners. The exemplary PSR cover 154 also includes an inner surface 216 and a third connector 217, which consists of latching protrusions 218a-218c that extend inwardly from the inner surface and are configured to mate with the first and second connectors 186 and 188 defined by the protrusions and indentations in the side walls 182 and 184 of housing main portion 150. The latching protrusions 218*a* and 218*b* are on the side wall 204 and the latching protrusion 218*c* is on the side wall 206. The latching protrusions may be integrally formed with, or separate structures that are secured to, the cover side walls. The first and third connectors 186 and 217 will cooperatively latch the housing main portion 150 and PSR cover 154 to one another when the PSR cover is in the first orientation, and the second and third connectors 188 and 217 will cooperatively latch the housing main portion and PSR cover to one another when the PSR cover is in the second orientation.

Turning to FIG. 14, which shows the housing main portion 150 and the PSR cover 154 in the latched state and the PSR cover in the first orientation relative to housing main portion, the latching protrusions 218*a*-218*c* are located in the primary indentations 190 and 200 and are axially aligned (i.e. aligned in the direction that the PSR cover moves on/off the housing main portion) with the protrusions 196*a*-196*c*. Accordingly, in the first orientation, the housing main portion 150 and the PSR cover 154 are latched to one another by way of the protrusions 196*a*-196*c* of the first connector 186 and the protrusions 218*a*-218*c* of the third connector 217. The second connector 188 is not connected to the third connector 217 in this orientation.

To that end, and referring to FIGS. 15-17, the latching protrusions 218*a*-218*c* in the illustrated embodiment (218*c* shown) each include cam surfaces 220 and 222 and each of the protrusions 196*a*-196*c* and 198*a*-198*c* on the side walls 182 and 184 includes cam surfaces 224 and 226. The resilience of the PSR cover 154 allows the side walls 204 and 206 to deflect as the cover moves from the unlatched state to the latched state and from the latched state to the unlatched state. The distance that each of the side walls 204 and 206 must deflect to clear the protrusions 196*a*-196*c* is represented by D1 in FIGS. 15-17 and the distance that each of the side walls must deflect to clear the protrusions 198*a*-198*c* is represented by D2 in FIGS. 19 and 20, which is less than distance D1. The first orientation is relatively high removal force orientation because the first connector protrusions 196*a*-196*c* protrude further in the radial direction (i.e. protrude further in a direction that is perpendicular to the direction that the PSR cover moves on/off the housing main portion) than the second connector protrusions 198*a*-198*c*.

As the PSR cover 154 moves in the direction of arrow A from the removed and unlatched state toward the housing main portion 150 (FIG. 15), the cam surfaces 222 on the protrusions 218*a*-218*c* of the cover (or "third") connector 217 will engage the edges 224 of the protrusions 196*a*-196*c* on the housing main portion first connector 186. As the PSR cover 154 continues to move in this direction (FIG. 16), the cover walls 204 and 206 will deflect radially outwardly, as permitted by the resilience of the PSR cover 154, by the distance D1 while the protrusions 218*a*-218*c* pass the edges 224. The PSR cover walls 204 and 206 will remain deflected radially outwardly until the protrusions 218*a*-218*c* are aligned with the primary indentations 190 and 200. At this point, the resilience of the PSR cover 154 will cause the walls 204 and 206 to move radially inwardly such that the protrusions 218*a*-218*c* are located within the primary indentations 190 and 200 (FIG. 17), in their radially retracted positions against the cam surfaces 226 of the protrusions 196*a*-196*c*, thereby latching the cover to the housing main portion. Conversely, when the PSR cover 154 pulled in the opposite direction (note arrow B in FIG. 17), the cam surfaces 220 on the protrusions 218*a*-218*c* will engage the cams surfaces 226 of the protrusions 196*a*-196*c*. The cover walls 204 and 206 will deflect radially outwardly by distance D1, to their radially extended positions, and the protrusions 218*a*-218*c* will move out of the primary indentations 190 and 200 as the PSR cover 154 continues to be pulled away from the housing main portion 150, thereby unlatching the cover.

In the second (or "relatively low removal force") orientation, which is illustrated in FIG. 18, the PSR cover 154 is rotated 180 degrees relative to the first orientation. The protrusions 218*a*-218*c* are located in the primary indentations 190 and 200 and are axially aligned with the protrusions 198*a*-198*c* (protrusion 218*c* shown). Accordingly, in the second orientation, the housing main portion 150 and the PSR cover 154 are latched to one another by way of the protrusions 198*a*-198*c* of the housing main portion second connector 188 and the protrusions 218*a*-218*c* of the cover (or "third") connector 217.

As the PSR cover 154 moves in the direction of arrow A from the removed and unlatched state toward the housing main portion 150 (FIG. 19), the cam surfaces 222 on the cover protrusions 218*a*-218*c* will engage the edges 224 of housing main portion protrusions 198*a*-198*c*. As the PSR cover 154 continues to move in this direction, the cover walls 204 and 206 will deflect radially outwardly, as permitted by the resilience of the PSR cover 154, by the distance D2 while the protrusions 218*a*-218*c* pass the edges 224. The PSR cover walls 204 and 206 will remain deflected radially outwardly until the protrusions 218*a*-218*c* are aligned with the primary indentations 190 and 200. At this point, the resilience of the PSR cover 154 will cause the walls 204 and 206 to move radially inwardly such that the protrusions 218*a*-218*c* are located within the primary indentations 190 and 200 (FIG. 20), in their radially retracted positions against the cam surfaces 226 of the protrusions 198*a*-198*c*, thereby latching the cover to the housing main portion. Conversely, when the PSR cover 154 pulled in the opposite direction (note arrow B in FIG. 20), the cam surfaces 220 on the protrusions 218*a*-218*c* will engage the cams surfaces 226 of the protrusions 198*a*-198*c*. The cover walls 204 and 206 will deflect radially outwardly by distance D2, to their radially extended positions, and the protrusions 218*a*-218*c* will move out of the primary indentations 190 and 200 as the PSR cover 154 continues to be pulled away from the housing main portion 150, thereby unlatching the cover from the housing main portion. As alluded to above, the distance D2 is less than distance D1 and, accordingly, less force required to deflect the PSR cover 154 (and latch and unlatch the cover from the housing main portion) in the second orientation than in the first orientation. It should also be noted that the first connector 186 is not connected to the third connector 217 in this orientation.

With respect to the deflection of the PSR cover walls, it should be noted that the first and second connectors 186 and 188 and third connector 217 in the illustrated embodiment are located in the longitudinally central region of the housing side walls 182 and 184 and PSR cover side walls 204 and 206. The longitudinally central region of the PSR cover side walls 204 and 206 is the region of maximum radial extension. Suitable resilient materials for the PSR cover 154 include, but are not limited to, a polycarbonate (PC)/acrylonitrile butadiene styrene (ABS) resin. Such materials, in combination with a wall thickness of about 0.050 inch and the other dimension of the cover described herein will allow the PSR cover 154 to resiliently deflect in the manner described above.

The main portion 150 and control portion 152 of the exemplary housing 106 may be formed from materials including, but not limited to, PCs, ABSs, PC/ABS blends, nylon and various combinations thereof. One specific example is Lexan® Resin HP1 R, from SABIC Innovative Plastics Company. Another specific example is Noryl® PPO, a modified polyphenylene oxide. In one exemplary implementation, the main portion 150 may include a main structure formed from Lexan® Resin HP1 R and a decorative overmold formed from a platable grade of PC/ABS with a chrome plating on the PC/ABS. In other implementations, the housing main portion 150 and control portion 152 may be formed from the same materials as the PSR cover 154, but will be stiffer due to the geometry.

Although the present connects are not limited to any particular dimensions unless such dimension are set forth in the claims below, the dimensions associated with the exemplary first and second connectors 186 and 188 are as follows. The depth of the primary indentations 190 and 200 (measured from the outer surface of the side walls 182 and 184) may be about 0.40 mm to 0.60 mm in some embodiments and are about 0.50 mm in the illustrated embodiment; the depth of the secondary indentations 192, 194 and 202 (measured from the outer surface of the side walls 182 and 184) may be about 0.25 mm to 0.45 mm in some embodiments and are about 0.35 mm in the illustrated embodiment; the length of the protrusions 196a-196c may be equal to the depth of the primary indentations 190 and 200, i.e. may be about 0.40 mm to 0.60 mm in some embodiments and are about 0.50 mm in the illustrated embodiment, or may be greater or less than the primary indentation depths; and the length of the protrusions 198a-198c may be equal to the depth of the primary indentations 190 and 200 less the depth of the secondary indentations 192, 194 and 202, i.e. may be about 0.25 mm to 0.45 mm in some embodiments and are about 0.35 mm in the illustrated embodiment, of may be of greater or lesser values.

It should be emphasized here that the latch apparatus described above is merely one example of an apparatus that may be used to secure the PSR cover 154 to the housing main portion 150. By way of example, but not limitation, an alternative PSR cover and housing main portion arrangement may be configured such that the locations of the above-described protrusions, indentations, cam surfaces and edges are reversed. Here, the PSR cover would include indentations that receive protrusions on the housing main portion. Also, instead of protrusion size, the angles of the cam surfaces may be used to control the amount of force required to latch and unlatch the cover. Another alternative is to simply include protrusions on one of the cover side walls 204 and 206, and reconfigure the housing connectors accordingly. A latch apparatus similar to that described above may also be associated with the portion of the housing above (in the illustrated orientation) the seal and with the open end of the PSR cover, i.e. located on the other side of the seal. The protrusions and indentations may also have curved surfaces instead of the linear surfaces illustrated in, for example, FIGS. 16 and 17.

The exemplary sound processor 100 may also be configured for use in or around water and, accordingly, configured so as to insure that the power supply receptacle 118 is waterproof. In the illustrated embodiment, a seal 228 is carried on the housing main portion 150 in the manner illustrated in FIG. 21. Generally speaking, the exemplary seal 228 may be a resilient band that extends around the entire perimeter of the housing main portion 150 and contacts the entire perimeter of the inner surface of the PSR cover 154, i.e. without gaps or "uninterrupted," with a relatively constant force that is sufficient to prevent ingress of liquid. Although the seal 228 is removable and replaceable, it is held in the illustrated location during use. It should also be noted that the seal 228 is compressed radially when the PSR cover 154 is moved from the open state (FIG. 21) where the power supply receptacle is accessible to the latched/covered state (FIGS. 14 and 18) where the power supply receptacle is not accessible. Put another way, the seal 228 is compressed in a direction (note arrows C) that is perpendicular or at least substantially perpendicular to the direction that the PSR cover 154 moves as it slides onto the housing main portion 150 and over the seal (note arrow A). The use of the phrase "radial compression" does not, however, impart a shape limitation on the housing and, in particular, does not require the housing to be circular or otherwise curved.

The exemplary seal 228 has one or more portions that deflect and one or more open spaces (or "air gaps") into which the portions can deflect during radial compression. In other words, at least one portion of the seal compressed into an air gap that was not previously occupied by seal material. So configured, less force is required to radially compress the present seal a particular distance as compared to a seal that is solid in cross-section. Thus, a seal that is the same or better (e.g. without yield and variations in compression force) may be achieved while at the same time reducing the amount of force required to move the PSR cover 154 from the open state to the latched state.

Figure 11:
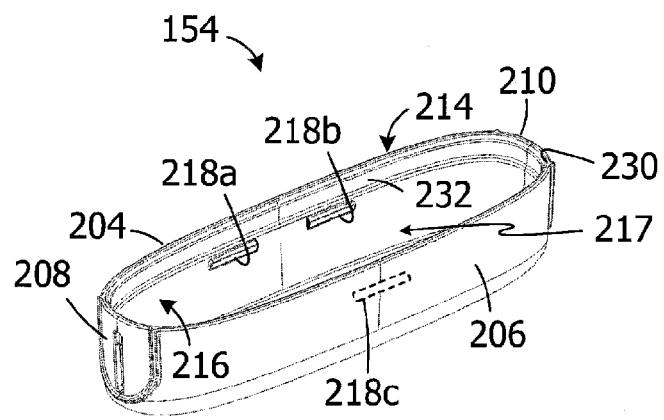
FIG. 11 is a perspective view of a power supply receptacle cover in accordance with one embodiment of a present invention.
Figure 12:
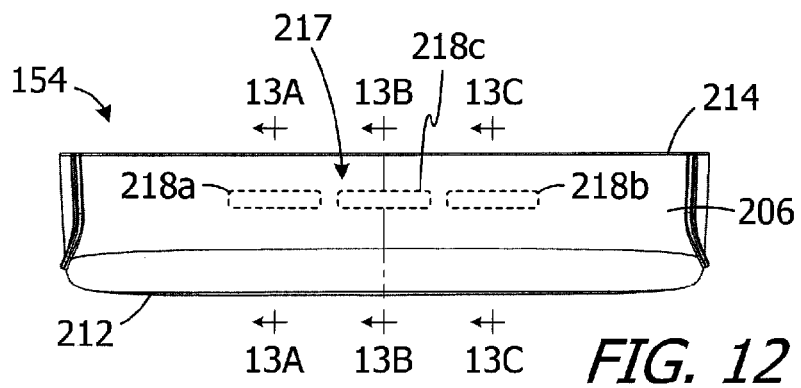
FIG. 12 is a side view of a power supply receptacle cover in accordance with one embodiment of a present invention.
Figure 13A:
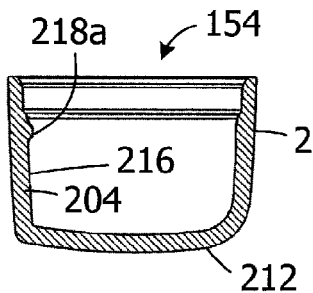
FIG. 13A is a section view taken along line 13A-13A in FIG. 12.
Figure 13B:
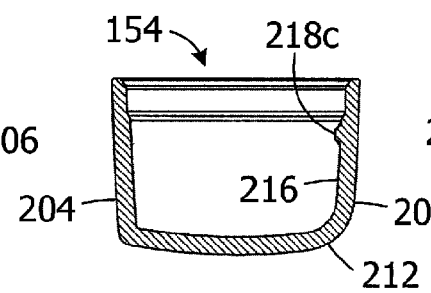
FIG. 13B is a section view taken along line 13B-13B in FIG. 12.
Figure 13C:
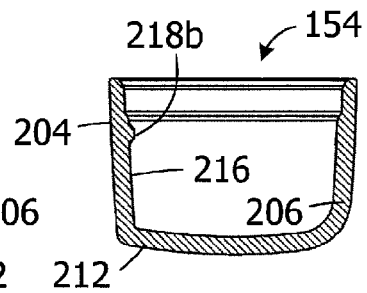
FIG. 13C is a section view taken along line 13C-13C in FIG. 12.

In at least some implementations, the configuration of the PSR cover 154 is such that it facilitates the controlled radial compression of the seal 228. Referring to FIG. 11, the inner surface 216 has a tapered transition portion 230 and a seal portion 232 that extend completely around the perimeter of the cover. The circumference of the inner surface 216 is greatest at the open end 214, then decreases through the transition portion 230 such that the slope is about 1.0 to about 1.7, and then is substantially constant in the seal portion 232. The transition portion 230 and seal portion 232 cooperate with the seal 228 in the manner described below with reference to FIGS. 24 and 25.

As illustrated in FIGS. 22 and 23, the exemplary seal 228 includes a base member 234, which defines the inner surface 236 of the seal, and a plurality of protrusions 238-242 that extend outwardly from the base member and have longitudinal ends 238a-242a. The seal 228 is formed from resilient material (discussed below) and, as is illustrated in FIG. 22, defines a closed geometric overall shape (e.g. circular or the illustrated oval) with an axis A. "Radial compression" is compression in a direction that is perpendicular to the axis A, "radial force" is force that is applied in a direction that is perpendicular to the axis A, and a "radial direction" is a direction that is perpendicular to the axis A. The seal 228 is slightly smaller than the portion of the housing main portion 150 on which is it is to be supported. As a result, the seal 228 will be pre-stressed when placed on the housing to prevent ingress of liquid between the seal inner surface 236 and the housing. The exemplary seal 228 also includes material-free regions 244 and 246 that are respectively located between protrusions 238 and 240 and protrusions 240 and 242. The material free regions 244 and 246 provide open spaces (or "air gaps") into which portion of the seal deflects during the slide-on radial compression that occurs when the PSR cover 154 is secured to the housing main portion 150.

To that end, FIG. 23A shows a cross-section taken in a plane that extends through the Axis A as a portion of the seal is exposed to radial force $F_R$ in the manner described below with reference to FIGS. 24-25. The radial force $F_R$ deflects the protrusions 240 and 242 into the material free regions 244 and 246 (FIG. 23). There are, at least during the radial compression, open spaces OS located between (in the radial direction) the points at which the radial force $F_R$ is being applied and the inner surface 236 of the seal 228 and/or the outer surface of the portion of the housing on which the seal is supported. The open spaces OS remain after the radial compression is complete in the illustrated implementation. The open spaces OS in the illustrated implementation are also located between (in the radial direction) the outer surface 248 of the seal base member 234 and the deflected protrusions 240 and 242. The deflected protrusions fold into available space providing outward radial loading which dynamically adjusts to fit into the available space.

Although the protrusions 238-242 are generally planar structures that extend radially outwardly and are perpendicular to the base member inner surface 236 in the illustrated embodiment, other configurations may be employed.

Figure 24:
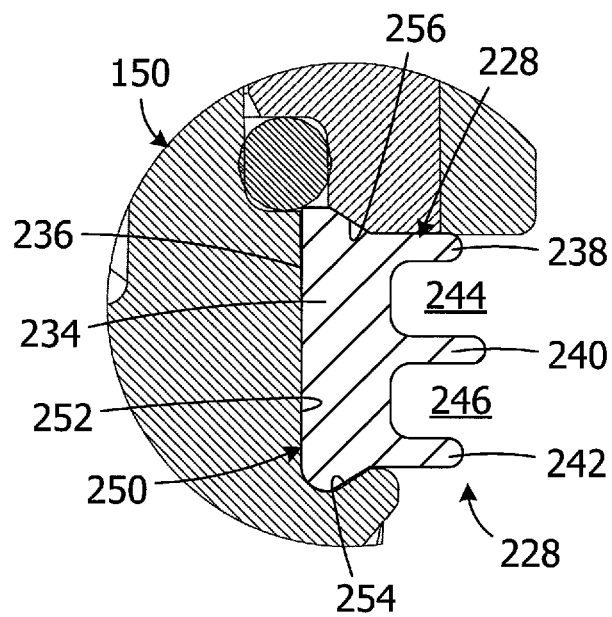
FIG. 24 is a section view of a portion of a sound processor in accordance with one embodiment of a present invention with the power supply receptacle cover removed.
Figure 25:
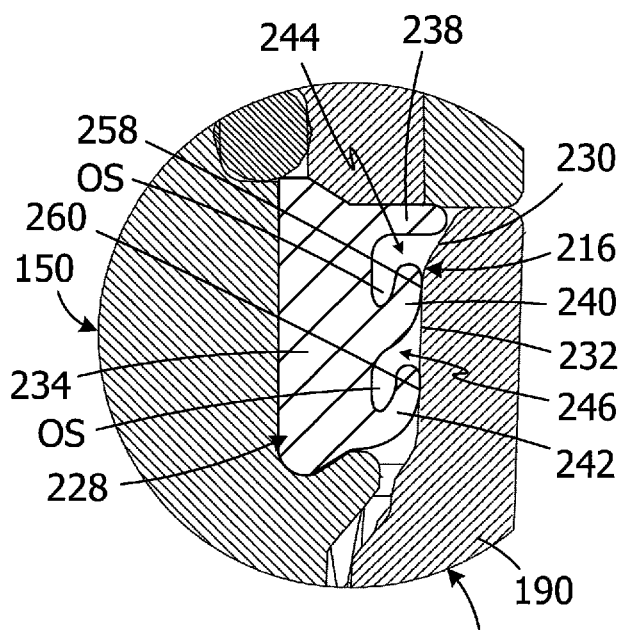
FIG. 25 is a section view of a portion of a sound processor in accordance with one embodiment of a present invention with the power supply receptacle cover in the latched position.

Turning to FIG. 24, the exemplary housing main portion 150 has a channel 250 into which the seal 228 may be inserted. The channel 250 has an inner surface 252 that abuts the seal inner surface 236. The channel 250 also has a pair of inwardly projecting surfaces 254 and 256. The seal main portion 234 has corresponding surfaces 255 and 257 (FIG. 23). The seal 228 is stretched and deflected into the channel 250 during assembly and held in the channel 250 by the inwardly projecting surfaces 254 and 256. So arranged, the protrusions 238-242 will extend radially outwardly from the main portion 234 and one or more of the protrusion will be located within a region 228 that will ultimately be occupied by a portion of the PSR cover 154. As the PSR cover 154 in the exemplary implementation moves toward the latched state, the inner surface transition portion 230 will sequentially engage and deflect the protrusions 242 and 240. When the PSR cover 154 reaches latched/covered state, which is illustrated in FIG. 25, the protrusions 240 and 242 will be deflected in the manner shown such that they engage the inner surface seal portion 232 at contact points 258 and 260 and there are open spaces OS between the protrusions and the main portion 234. Each contact point 258 and 260, which are the points at which the radial force $F_R$ (FIG. 23A) is applied to the seal 228, extends around the perimeter of the PSR cover 154 with enough force to prevent ingress of fluid.

It should be noted here that gradually deflecting the protrusions 240 and 242 with the transition portion 230 of the exemplary PSR cover inner surface 216, as opposed to the more abrupt deflection that would occur if the seal portion 232 extended all the way to the open end 214, provides a number of beneficial results. For example, the deflection of the protrusions 240 and 242 in the exemplary seal 228 occurs in a gradual manner. The protrusions 240 and 242 are deflected axially and radially by the transition portion 230 and then radially by the seal portion 232. As such, the radial force applied to the seal, as well as the axial resistance that the user experiences, increases in a gradual manner and the transition from the detached/open state to the attached/covered state is smooth.

Figure 26:
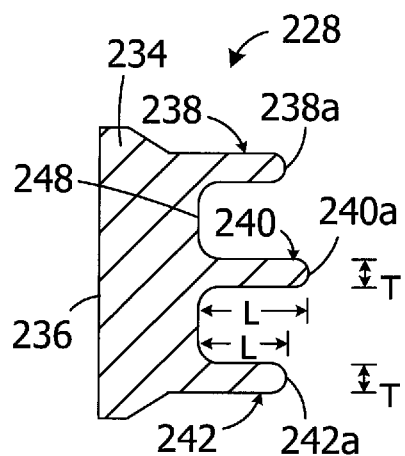
FIG. 26 is a section view of a seal in accordance with one embodiment of a present invention.

Although the protrusions 238-242 may be identical in some implementations, the protrusion 240 in the exemplary seal 228 is configured so as to have different structural characteristics than the protrusions 238 and 242. The differences in structural characteristics are differences that result in differences in sealing characteristics generally, and the creation of more sealing force at protrusion 240 in particular. Referring to FIG. 26, in the exemplary seal 228, the length L of the protrusion 240 is greater than the length of protrusion 242, while the thicknesses T of protrusions 240 and 242 are same. Given the fact that the distance between the seal base member 234 and the seal portion 230 of the PSR cover inner surface 216 is essentially the same at each protrusion, and referring to FIG. 25, the protrusion 240 will undergo a greater degree of deflection and radial compression than the protrusion 242 because it is longer. As such, as despite the fact that the protrusions are the same thickness and formed from the same materials, the protrusion 240 will form a tighter seal than the protrusion 242 and will act as the primary portion of the seal. Locating the primary portion of the seal sufficiently away from the open end 214 is advantageous for insuring that the seal makes uniform radial contact with the PSR cover inner surface 216. The protrusion 242 functions as the secondary portion of the seal to prevent ingress of liquid should liquid pass the seal formed by protrusion 240. Such liquid will be at a lower pressure than liquid at the seal formed by protrusion 240.

It should be noted here that, given the respective dimensions of the protrusion 238 and the inner surface transition portion 230, the protrusion 238 does not create a seal or at least any substantial seal. The protrusion 238 may, therefore, be omitted in some embodiments. The protrusion 238, which is identical to protrusion 242, is included in the exemplary seal 228 for a number of other reasons. Most notably, the inclusion of the protrusion 238 makes the seal 228 symmetric about the protrusion 240 and, accordingly, it is reversible. If the seal 228 is mounted "upside down" on the housing 106, there will be no change in function and, in some instances, the life of the seal may be extended if it is removed and reversed after some period of use. The beam strength of the seal 228, as defined by the material thickness in the radial direction, is symmetric in the axial dimension. The additional beam strength associated with the protrusion 238 also improves the seal between the inner surface 236 and the inner surface 252 of the housing channel 250 created by the pre-stressing of the seal.

Figure 27:
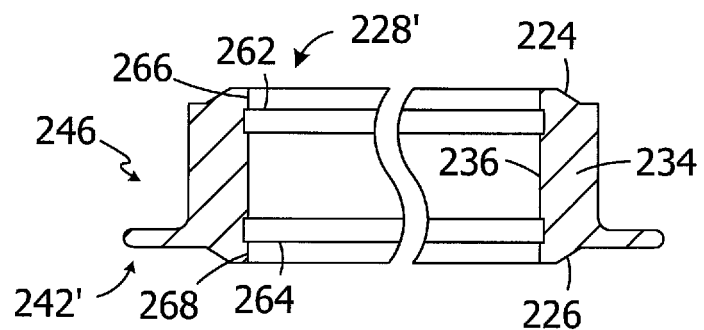
FIG. 27 is a section view of a seal in accordance with one embodiment of a present invention.
Figure 31:
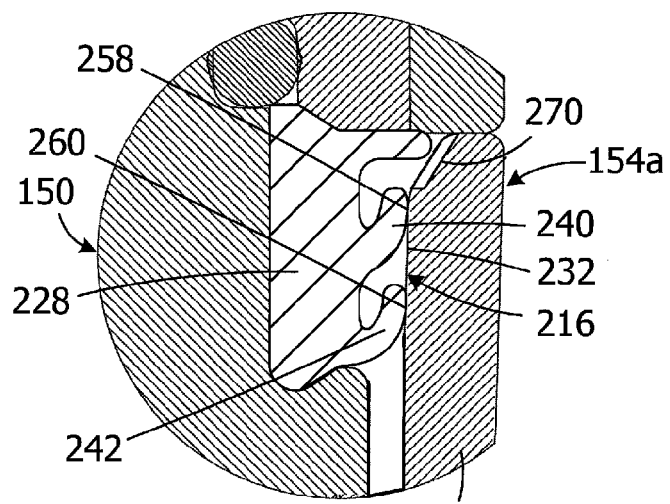
FIG. 31 is a section view of a portion of a sound processor main portion with the power supply receptacle cover illustrated in FIG. 31 in place.

The exemplary seal 228' illustrated in FIG. 27, which is otherwise identical to seal 228 and may be used in place of the seal 228 in the sound processor 100, includes only a single protrusion 242', a single material free region 246, and one or more grooves, e.g. grooves 262 and 264, that are formed in the base member 234. The single protrusion 242' forms a seal in the manner described above in the context of protrusion 240 (FIG. 25) and, in the illustrated embodiment, the single protrusion is the same length as the protrusion 240. In embodiments that include the seal 228', the inner surface of the associated PSR cover may include a tapered transition portion (e.g. transition portion 230 in FIG. 24), or as is illustrated in FIG. 31, the tapered transition portion may be omitted.

The grooves 262 and 264 are relatively shallow (e.g. about 0.004 inch), extend around the perimeter of the inner surface 236, and define relatively small (as compared to the entire surface 236) upper and lower contact surfaces 266 and 268 at the axial ends of the base member 234. The separate seals between the inner surface 236 and the inner surface 252 of the housing channel 250 formed at the spaced contact surfaces 266 and 268 are, in some instances, more readily controllable than a single seal formed from an inner surface without grooves. Although the exemplary grooves 262 and 264 are rectangular in shape, grooves of other shapes may be employed. It should also be noted that grooves, such as grooves 262 and 264, may be added to the inner surface of the seal embodiments described above if so desired.

With respect to materials, suitable resilient materials for the exemplary seals disclosed herein include, but are not limited to, silicone. The dimensions of the seals will depend on the desired characteristics and the dimensions of the housing main portion and PSR cover, and the present seals are not limited to any particular dimensions unless such dimension are set forth in the claims below. Referring to FIG. 22, the unstretched major and minor dimensions (measured perpendicular to the Axis A) of the exemplary seal 228 are about 53.00 mm to 57.00 mm and about 14.00 mm to 16.00 mm. Referring to FIG. 26, the thickness of the base member 234, i.e. the distance between inner surface 236 and outer surface 248, is about 0.90 mm to 1.00 mm, the height of the base member is about 2.80 mm to 3.80 mm, the protrusions 238-242 are about 0.30 mm to 0.50 mm thick, the protrusions 238 and 242 are about 0.80 mm to 1.00 mm long, and the length of protrusion 240 is about 1.0 mm to 1.20 mm.

The PSR cover and seal arrangements described above are such that the waterproof rating at the PSR cover will be IPX7, i.e. there will be no ingress of visible water into the power supply receptacle 118 when the sound processor 100 is immersed in water at a depth of 1 meter for 30 minutes.

The overall configuration of the housing 106 may also be such that the PSR cover 154 is a child resistant cover. In particular, the dimensions of the housing 106 and the location of the latching apparatus make it exceedingly difficult for a young child (e.g. infants and toddlers up to about 4 years of age) to remove the PSR cover 154. Put another way, the overall dimensions of the housing 106 may be used, in addition to the placement of the PSR cover 154 in the first orientation, to make it more difficult for a child to remove the PSR cover.

Figure 28:
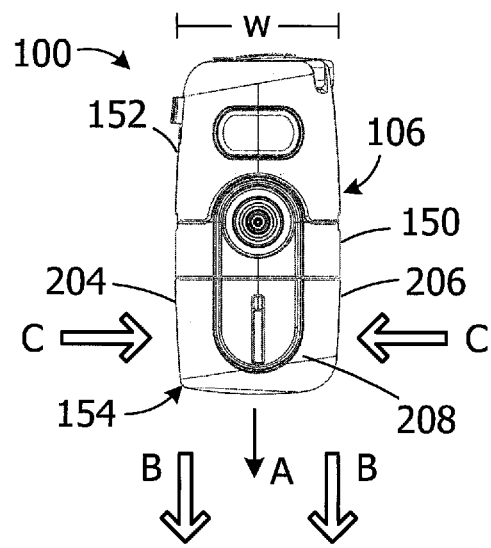
FIG. 28 is an end view of a sound processor in accordance with one embodiment of a present invention.
Figure 29:
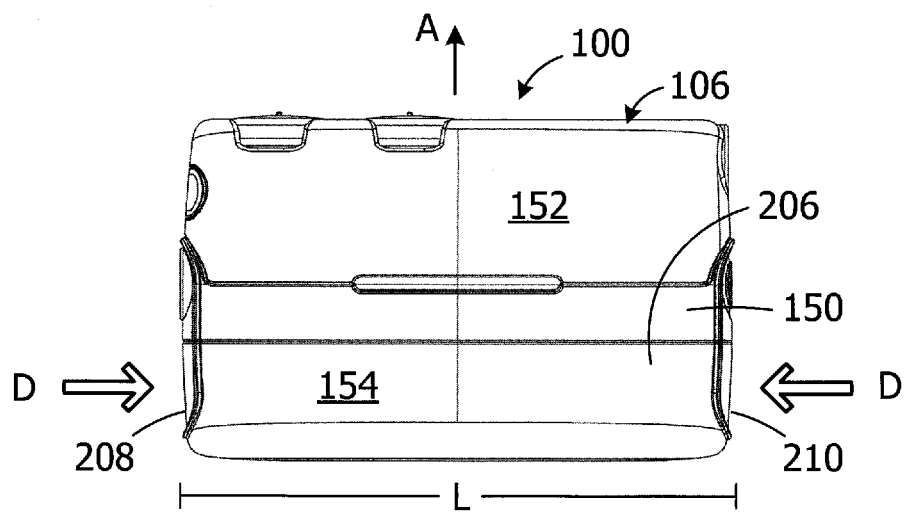
FIG. 29 is a side view of a sound processor in accordance with one embodiment of a present invention.

Referring to FIGS. 28-29, in the illustrated embodiment, the length L of the housing 106 is substantially greater than, e.g. at least about two times and in some instances at least about three times, the width W of the housing. The length L of the exemplary housing 106 is also relatively large. The "length" is the major dimension perpendicular to the axis A which, in the illustrated embodiment, is also perpendicular to direction of cover movement (note arrows B in FIG. 28). As used herein, "relatively large" means at least 2 inches, which is a length that a young child would find difficult to grip with sufficient force to remove the PSR cover 154. Exemplary values of the length L range from about 2 inches to about 4 inches, depending on the age of the child, and the illustrated embodiment is 2.3 inches long. The width W of the exemplary housing 106 is relatively small. The "width" is the minor dimension perpendicular to the axis A which, in the illustrated embodiment, is also to the direction of cover movement. As used herein, "relatively small" means no more than 2 inches (e.g. when the length is 4 inches). Exemplary values of the width W range from about 0.25 inch to about 2 inches, and the illustrated embodiment is about 0.7 inches wide. The lengths of the housing main portion side walls 182 and 184 and the PSR cover side walls 204 and 206 closely correspond to, or are the same as, the length L of the housing 106, while the lengths of the housing main portion end walls 178 and 180 and the PSR cover end walls 208 and 210 closely correspond to, or are the same as, the width W of the housing 106. As noted above, the wall thickness of the PSR cover 154, in combination with the resiliency of the cover materials, facilitates the resilient radial deflection of the side walls 204 and 206.

Given the configuration described in the preceding paragraph, its would be extremely difficult, as well as counterintuitive, for a young child to grip the PSR cover at the end walls 208 and 210. The distance between the end walls 208 and 210 is too great to fit within a young child's hand. Instead, when attempting to pull the PSR cover 154 from the housing main portion 150, a young child will grip the PSR cover 154 at the side walls 204 and 206. The distance between side walls 204 and 206 is considerably smaller and, accordingly, they are easier to grip. A gripping force in the direction of arrows C (FIG. 28) will be applied to the side walls 204 and 206 when applying removal force in the direction of arrows B. Applying gripping force in the direction of arrows C will, however, prevent the protrusions 218a-218c, which are carried by the PSR cover side walls 204 and 206 from moving out of the indentations 190 and 200. The gripping force prevents the PSR cover side walls 204 and 206 from moving radially outwardly. As the young child pulls harder in the direction of arrows B, he/she will also apply more force in the direction of arrows C to maintain a grip on the cover 154, thereby preventing the protrusions 218a-218c from coming out of the indentations 190 and 200 despite the increase in the pulling force that would otherwise deflect the side walls 204 and 206 radially outwardly.

When an adult who is aware of the present configuration desires to remove the PSR cover 154 from the housing main portion 150, he/she will grip the cover at the end walls 208 and 210 and apply a gripping force in the direction of arrow D (FIG. 29) and removal force in the direction of arrows E (FIG. 28). The cam surfaces 220 on the protrusions 218a-218c will engage the cam surfaces 226 of the protrusions 196a-196c (or 198a-198c) as the cover 154 moves in the direction of arrows B. Because there is no gripping force preventing the cover walls 204 and 206 from deflecting radially outwardly, the protrusions 218a-218c will move out of the indentations 190 and 200 as the PSR cover 154 in the direction of arrows B, thereby unlatching the cover and permitting removal.

PSR covers may also be provided with structures that facilitate movement of the PSR cover to and from the attached/covered state (FIG. 18). More specifically, the robust seal provided by the seal 228 (or 228') may trap air within the power supply receptacle 118 as the PSR cover 154 approaches the attached/covered state during placement of the PSR cover over the power supply receptacle. The pressure of the air (if trapped) will then increase as the PSR cover 154 continues its movement to the attached/covered state, thereby creating a force that opposes the force being applied by the user. Similarly, when the user pulls the PSR cover 154 from the attached/covered state at the outset of the removal process, a suction force that is created by the trapped air will oppose removal of the PSR cover until the PSR cover has moved a distance sufficient to break the seal.

Figure 30:
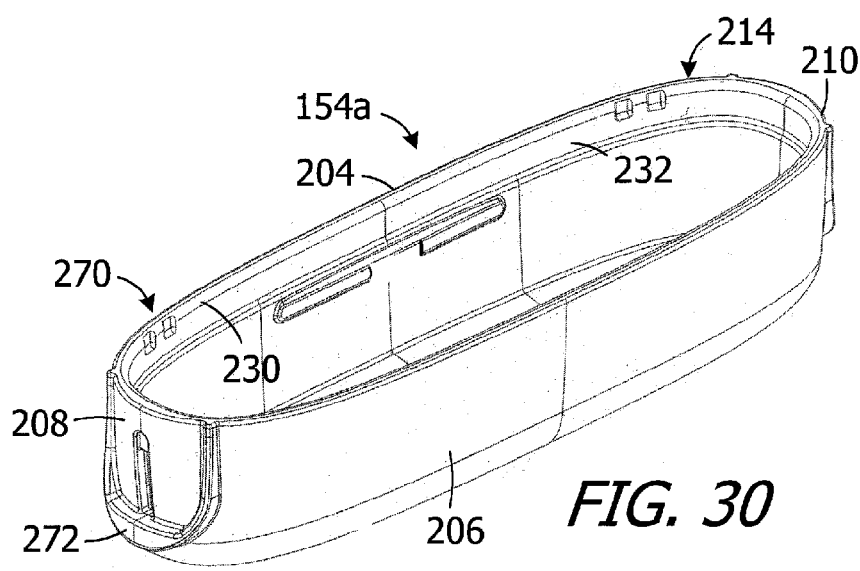
FIG. 30 is a perspective view of a power supply receptacle cover in accordance with one embodiment of a present invention.

One example of a PSR cover that is configured to vent air without effecting the seal provided by seal 228, and which may be incorporated into any of the sound processors described herein, is generally represented by reference numeral 154a in FIGS. 30 and 31. PSR cover 154a is essentially identical to PSR cover 154 and similar elements are represented by similar reference numerals. The PSR cover 154a also includes one or more vents. The vents may be of any suitable number, form or location. There are four sets of two vents 270 in the illustrated embodiment, with two sets on each side wall 204 and 206. The sets of vents 270 may be located at the same locations on the side walls 204 and 206, as they are in the exemplary embodiment, or may be at different locations.

In the illustrated embodiment, the vents 270 are located in the tapered transition portion 230 and, accordingly, do not effect the seal formed between the cover inner surface seal portion 232 and the seal protrusion 240 (FIG. 31) at contact point 258. However, during placement of the PSR cover 154a onto the housing main portion 150, the vents 270 permit air passage past the seal protrusion 240 and prevent the aforementioned pressure increase within the power supply receptacle 118. Similarly, after the PSR cover 154a has been moved a small distance from the attached/covered state during cover removal, the vents 270 will be aligned with the seal protrusion 240 so that air can be drawn into the power supply receptacle 118, thereby preventing the creation of suction force.

It should also be noted that the vents 270 are located near both longitudinal ends of each of the cover side walls 204 and 206 in the illustrated embodiment. Thus, should the PSR cover 154a be tilted relative to housing main portion 150 when the being placed on the main portion, i.e. should one of the end walls 208 and 210 be closer to the main portion than the other, venting will occur at the trailing vents 270 as the PSR cover straightens out prior to reaching the attached/covered state. Similarly, venting will occur if the user pulls from one end of the PSR cover 154*a* during removal. Venting will occur at all vents 270 during placement and removal when the PSR cover 154*a* is not tilted relative to the housing main portion 150.

Figure 32:
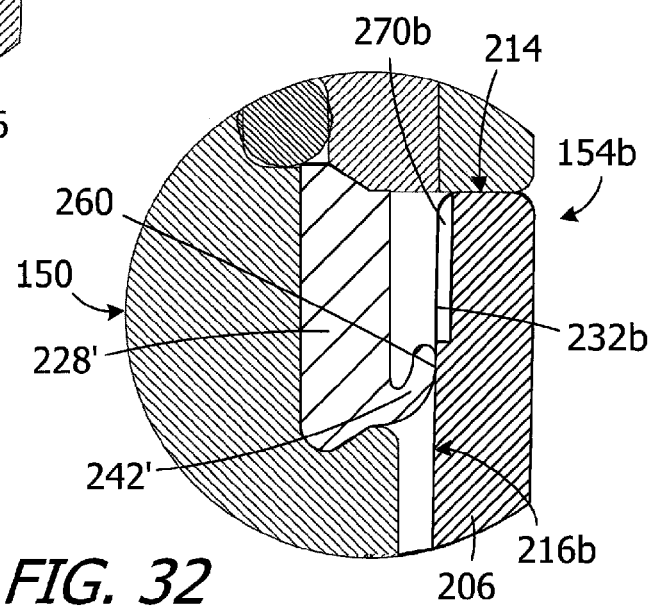
FIG. 32 is a section view of a portion of a sound processor main portion with the power supply receptacle cover in place.

The exemplary cover 154*b* illustrated in FIG. 32 is essentially identical to PSR cover 154*a* and similar elements are represented by similar reference numerals. Here, however, the cover 154*b* is configured for use with seal 228'. To that end, the cover includes an inner surface 216*b* without a tapered transition portion. The seal portion 232 extends essentially to the open end 214. The single protrusion 208' forms a seal at contact point 260.

To facilitate movement of the PSR cover 154*b* to and from the attached/covered state, the PSR cover also includes vents 270*b* that may be of any suitable number, form or location. There may be four sets of two vents 270*b*, as is described above with reference to vents 270, with the vents being long enough to extend from about the open end 214 to the illustrated location adjacent to the contact point 260.

The exemplary PSR cover 154*a* illustrated in FIGS. 30 and 31 also includes a protrusion 272 on the cover end walls 208 and 210. The protrusions 272, which help the user grip the end walls 208 and 210, may also be employed on the PSR covers 154 and 154*b*.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A sound processor for use with a cochlear implant, the sound processor comprising:
   a housing including
   a main portion defining a power supply receptacle,
   a power supply receptacle (PSR) cover movable between an uncovered state where the power supply receptacle is accessible and a covered state where the power supply receptacle is not accessible,
   the main portion and PSR cover being respectively configured such that the PSR cover may be in the covered state in a first orientation relative to the main portion and may be in the covered state in a second orientation relative to the main portion that is different than the first orientation, and
   a connector arrangement configured to connect the PSR cover to the main portion at a first connection force level when the PSR cover is in the covered state in the first orientation and to connect the PSR cover to the main portion at a second connection force level when the PSR cover is in the covered state in the second orientation;
   sound processor circuitry carried within the housing; and
   a communication device adapted to operably connect the sound processor circuitry to the cochlear implant.

2. A sound processor as claimed in claim 1, wherein the connector arrangement comprises a latch arrangement.

3. A sound processor as claimed in claim 1, wherein
   the connector arrangement includes first and second connectors on the main portion and a third connector on the PSR cover;
   the first and third connectors connect the PSR cover to the main portion when the PSR cover is in the covered state in the first orientation; and
   the second and third connectors connect the PSR cover to the main portion when the PSR cover is in the covered state in the second orientation.

4. A sound processor as claimed in claim 3, wherein
   the main portion includes a first side wall and a second side wall opposite the first side wall, portions of the first connector are associated with the first and second main portion side walls, and portions of the second connector are associated with the first and second main portion side walls; and
   the PSR cover includes a first side wall and a second side wall opposite the first side wall, and portions of the third connector are associated with the first and second PSR cover side walls.

5. A sound processor as claimed in claim 4, wherein
   the first connector includes protrusions on the main portion first and second side walls;
   the second connector includes protrusions on the main portion first and second side walls; and
   the third connector includes protrusions on the PSR cover first and second side walls.

6. A sound processor as claimed in claim 5, wherein the first connector protrusions are longer than the second connector protrusions.

7. A sound processor as claimed in claim 4, wherein
   the first connector includes indentations on the main portion first and second side walls;
   the second connector includes indentations on the main portion first and second side walls; and
   the third connector includes protrusions on the PSR cover first and second side walls.

8. A sound processor as claimed in claim 4, wherein
   the first connector includes two laterally spaced portions on the main portion first side wall and a single portion on the main portion second side wall;
   the second connector includes two laterally spaced portions on the main portion second side wall and a single portion on the main portion first side wall; and
   the third connector includes two laterally spaced portions on the PSR cover first side wall and a single portion on the PSR cover second side wall.

9. A sound processor as claimed in claim 1, wherein
   the first and second connection force levels comprise first and second levels of pulling force required to disconnect the PSR cover from the main portion.

10. A sound processor as claimed in claim 1, wherein the PSR cover first and second side walls are resiliently movable between a radially extended position and a radially retracted position and biased to the radially retracted position.

11. A sound processor as claimed in claim 1, wherein the length of the PSR cover is at least about two times the width of the PSR cover.

12. A sound processor as claimed in claim 1, wherein the communication device comprises a headpiece.

13. A sound processor, comprising:
   a housing including
   a main portion defining a power supply receptacle,
   a power supply receptacle (PSR) cover movable between an uncovered state where the power supply receptacle is accessible and a covered state where the power supply receptacle is not accessible, the main portion and PSR cover being respectively configured such that the PSR cover may be in the covered state in a first orientation relative to the main portion and may be in the covered state in a second orientation relative to the main portion that is different than the first orientation, and means for latching the PSR cover to the main portion at a first connection force level when the PSR cover is in the covered state in the first orientation and latching the PSR cover to the main portion at a second connection force level when the PSR cover is in the covered state in the second orientation;

sound processor circuitry carried within the housing; and a communication device adapted to operably connect the sound processor circuitry to a cochlear implant.

14. A sound processor as claimed in claim 13, wherein the first and second connection force levels comprise first and second levels of pulling force required to disconnect the PSR cover from the main portion.

15. A sound processor as claimed in claim 13, wherein the length of the PSR cover is at least about two times the width of the PSR cover.

16. A sound processor as claimed in claim 13, wherein the PSR cover first and second side walls are resiliently movable between a radially extended position and a radially retracted position and biased to the radially retracted position.

17. A sound processor as claimed in claim 13, wherein the communication device comprises a headpiece.

* * * * *